United States Patent [19]

Farer et al.

[11] Patent Number: 5,246,780
[45] Date of Patent: Sep. 21, 1993

[54] COATED PARTICLE FOR USE IN COSMETIC PREPARATIONS AND METHOD

[75] Inventors: Alan M. Farer, Morganville; Elisa L. Burdzy, Clifton; Fifi Hanna, Kearny; A. John Penicnak, Mountain Lakes, all of N.J.

[73] Assignee: L'Oreal, Paris, France

[21] Appl. No.: 751,701

[22] Filed: Aug. 29, 1991

[51] Int. Cl.$^5$ .................... A61K 7/021; A61K 7/035; B05D 7/22; B32B 15/02

[52] U.S. Cl. .................................. 428/404; 424/63; 424/69; 427/215; 427/222; 428/403; 428/405; 428/407; 514/60; 514/770; 514/784; 514/844

[58] Field of Search .............. 428/403, 404, 405, 407; 424/63, 69; 427/214, 215, 222; 514/60, 770, 784, 844

[56] References Cited

U.S. PATENT DOCUMENTS

| | | |
|---|---|---|
| 3,615,972 | 4/1967 | Morehouse et al. ............ 428/321.5 |
| 4,387,138 | 6/1983 | Gift ..................... 428/407 |
| 4,704,330 | 11/1987 | Moore et al. .................... 428/407 |
| 4,818,614 | 4/1989 | Fukui et al. .................... 428/407 |
| 4,877,604 | 10/1989 | Schlossman ........................ 424/63 |
| 4,988,502 | 9/1989 | Ounanian et al. ................. 424/63 |
| 4,988,503 | 1/1990 | Macchio et al. .................. 424/63 |
| 5,023,075 | 6/1991 | Macchio et al. .................. 424/69 |
| 5,030,446 | 1/1990 | Russ et al. ......................... 424/63 |
| 5,034,216 | 1/1990 | Barone et al. .................... 424/63 |
| 5,106,838 | 4/1992 | Reinhart .......................... 514/59 |

FOREIGN PATENT DOCUMENTS 0056219 7/1982 European Pat. Off. .
9002508 10/1991 France .

Primary Examiner—Paul J. Thibodeau
Assistant Examiner—D. S. Nakarani
Attorney, Agent, or Firm—Brumbaugh, Graves, Donohue & Raymond

[57] ABSTRACT

A coated particle useful in cosmetic compositions including a base particle, a coupling agent and an outer coating, and a method of making same. A preferred embodiment comprises hollow spherical polyvinylidene copolymer base particles, isopropyl tri-isostearyl titanate as the coupling agent and boron nitrate powder as the outer coating.

18 Claims, No Drawings

COATED PARTICLE FOR USE IN COSMETIC PREPARATIONS AND METHOD

BACKGROUND OF THE INVENTION

Cosmetic preparations have been used since early times to improve the appearance of the skin and hair. While most cosmetic products are relatively simple compositions, they contain many ingredients which are not truly compatible, easily processed or adherent to the skin. Components such as pigments are not easily dispersed into products with oil and water phases. In addition, cosmetic compositions such as cake eye shadow or blush require careful formulation to provide a compressible powder which will adhere to the skin. Manufacture of a pressed powder requires mixing, grinding and sifting operations which are energywise, relatively time consuming and costly.

In order to improve dispersion and related characteristics, cosmetic materials have been coated with lecithin (U.S. Pat. No. 4,988,502), low density polyethylene (U.S. Pat. No. 5,034,216) and titanates (U.S. Pat. No. 4,877,604).

In an alternate method, expensive additives, for example, boron nitride, along with hollow thermoplastic microspheres and N-acyl lysine derivatives are used to improve the processability of compressed powders (FR application No. 90 02508, filed Feb. 28, 1990).

While such methods have somewhat improved the properties and ease of dispersion of cosmetic components, it has been discovered that coating a cosmetic component onto a particle through the use of a coupling agent facilitates processing, lowers cost, and improves tactile properties.

It is an object of this invention to provide a coated particle for use in cosmetic preparations which is easily processed, reduces raw material costs, and enhances the aesthetic properties of cosmetic preparations.

SUMMARY OF THE INVENTION

This invention relates to a coated particle composition for use in cosmetic preparations comprising a base particle having an outer surface, a coupling agent attached to the outer surface of the base particle, and a boron nitride coating attached to the base particle through the coupling agent.

The invention also relates to a method for forming boron nitride coated particles for use in cosmetic preparations which comprises applying a first coating of a coupling agent selected from the group consisting of silanes and titanates to a base particle, and thereafter applying a coating of boron nitride as a second coating over the coupling agent.

The use of boron nitride in cosmetic preparations in the amount of 0.1 to 3% by weight has been found to facilitate manufacturing and improve tactile properties. Improved tactile properties include better adhesion to the skin, excellent emollient properties and an overall soft-to-the-touch quality. In addition, cosmetic preparations including boron nitride tend to exhibit a smoother, glossier texture. However, boron nitride is a costly and highly dense material. By utilizing boron nitride coated particles prepared according to this invention as opposed to neat boron nitride, lower amounts of boron nitride can be used to provide the same improvements in tactile properties to the finished cosmetic preparation without incurring higher costs. In this regard, coated particles having boron nitride bound to a base particle through the use of a coupling agent can be used to provide exceptional aesthetic properties to cosmetic preparations including powder products, mascaras, emulsions (including make-ups and moisturizers), lipsticks, eye liners, lip liners, creme blushers, nail enamels, creme make-ups, and make-up removers.

An alternate embodiment of this invention is a coated spherical polyvinylidene chloride copolymer particle composition for use in cosmetic preparations comprising a spherical polyvinylidene chloride copolymer base particle having a coupling agent selected from the group consisting of silanes and titanates attached to the outer surface of the particle and a coating attached to the spherical polyvinylidene copolymer base particle through the coupling agent. The use of coated spherical polyvinylidene chloride copolymer particles in cosmetic preparations enhances fluidity and dispersion of the cosmetic preparation.

The alternative embodiment of this invention also comprises a method of forming the coated spherical polyvinylidene chloride copolymer particles which comprises applying a first coating material to the particles which is a coupling agent selected from the group consisting of silanes and titanates, and thereafter applying a second coating material, other than coupling agent, to the particle.

The present invention further contemplates cosmetic compositions formulated to contain the coated particles of the invention, as described above.

DETAILED DESCRIPTION OF THE INVENTION

The coated particles of this invention, both those with spherical particles and those coated with boron nitride, have a particle size in the range of 5 to 250$\mu$, preferably 5–150$\mu$, most preferably 5–80$\mu$.

The coupling agents suitable for use in the invention are selected from the group consisting of silanes and titanates. Suitable titanates are described in U.S. Pat. No. 4,877,604 and include coordinate titanates such as tetraisopropyl (di(dioctyl) phosphito titanate, tetra (2, 2 diallyoxymethyl) butyl, di (ditridecyl) phosphito titanate, and monoalkoxy titanates such as isopropyl dimethacryl isostearoyl titanate. Most preferred is isopropyl triisostearoyl titanate.

The coupling agent can be applied to the base particle according to the methods described in U.S. Pat. No. 4,877,604. One method of applying coupling agent to the particle is to add 0.01 to 5.0 weight percent (of base particle weight), preferably 2%, liquid coupling agent to a uniform dispersion of base particles in suspension at room temperature under rapid stirring conditions for 30 to 60 minutes. An alternate method comprises spraying the liquid coupling agent onto a fluidized or agitated bed of particles.

Suitable base particles for coating with boron nitride include polypropylene, polycarbonate, silicone powder, cellulose, urea-formaldehyde resin, reticulated gelatin, collagen, keratin, silica, alumina, titanium dioxide, zinc oxide, zirconium oxide, calcium silicate, glass beads, stearates, mica and polyvinylidene chloride copolymer. Preferably, boron nitride is coated onto a particle of polyamide (Nylon), starch, polymethylmethacrylate, low density polyethylene, silica, polyvinylidene chloride copolymer or polystyrene, and it is further preferred that the base particles be coated first with a coupling agent. These base materials may be in the form of irregularly shaped particulates or spherical powders having a particle size of 2–200μ. The boron nitride is present at a level of 50% to 99% by weight, preferably 80 to 97% by weight of the coated particle. The most preferred form of boron nitride used for coating particles in accordance with this invention is hexagonal boron nitride having a particle size of 0.1 to 40μ. One suitable line of products are available as Combat ® boron nitride powders, from Standard Oil Engineered Materials Company, Niagara Falls, N.Y.; the high purity grades and specifically grade SHP325, are preferred.

Preferred base particles are hollow microspheres made of synthetic thermoplastic material such as polyvinylidene chloride copolymer having a particle size of 5 to 40μ and a specific density of 0.01 to 0.065 gm/cm$^3$. The hollow part of the microsphere is filled with a gas, typically a hydrocarbon. The hollow microspheres may be prepared according to known processes such as described in U.S. Pat. No. 3,615,972 and European Patent 056,219. The microsphere can be made of any non-toxic and non-irritant thermoplastic material. Suitable materials include polymers or copolymers of ethylene derivatives, polyethylene, polystyrene, copolymers of vinyl chloride-acrylonitrile, polyesters, polyamides, polymers of urea-formaldehyde, and copolymers of vinylidene chloride such as vinylidene chloride-acrylonitrile and the like.

Most preferred are hollow microspheres of polyvinylidene copolymer having a particle size less than 40μ, preferably 20μ max. and a density less 0.1 g/cm$^3$, preferably 0.01 to 0.065 g/cm$^3$, which are available from the Kemanord Plast Company under the trade name EXPANCEL 551 DE 20 (particle size 20μ max.) and EXPANCEL 551 DE (particle size 40μ max.). EXPANCEL is a tradename for a copolymer of vinylidene chloride-acrylonitrile.

These hollow polyvinylidene chloride spheres have an extremely low density and are normally difficult to process into a compressible cosmetic powder. By coating these spheres with a coupling agent and thereafter with boron nitride, a low density material is obtained which is easily dispersed in cosmetic preparations to give a product that is compressible, that adheres to the skin, and which has excellent tactile properties. Surprisingly, it has been found that cosmetic preparations containing boron nitride coated polyvinylidene chloride copolymer spheres have tactile and other properties which are superior to cosmetic preparations in which boron nitride and polyvinylidene chloride copolymer spheres are included as separate components. The products containing the coated hollow spheres are more dense, have lower oil absorption, improved skin adhesion, and improved compressibility. In addition, the coated spheres can be used at higher levels without processing difficulties.

While the most preferred coated particle is provided where boron nitride is coated onto hollow polyvinylidene chloride copolymer spheres, treated with a coupling agent, other suitable coatings for thus-treated polyvinylidene chloride copolymer spheres are certain commonly used cosmetic preparation ingredients including mineral, organic, or pearlescent pigments, silicone powders, Nylon, polytetrafluoroethylene, polypropylene, polystyrene, polymethylmethacrylate, lauroyl lysine, zinc stearate, starch, cellulose powder, collagen, keratin, reticulated gelatin, urea-formaldehyde resin, mica, talc, rare earth oxides, zinc oxide, zirconium dioxide, titanium dioxide, carbides of Ti, Zr, and Al, titanium nitride, barium sulfate, aluminum oxide, iron oxides, bismuth oxychloride and combinations thereof. These coatings are applied to the polyvinylidene spheres in an amount of 40% to 97% preferably 75–90% by weight of the coated particle.

By coating pigments onto coupling agent-treated polyvinylidene chloride copolymer hollow spheres, the pigments are much more easily dispersed in cosmetic preparations. As a further advantage, this procedure has the benefit of decreasing the bulk density of the pigment, so that when it is added as an ingredient to a fluid cosmetic preparation such as a fluid emulsion, the pigment is far less likely to separate out of the emulsion to cause discoloration or stiration in the product. Preferred pigment coated particles include titanium dioxide, black iron oxide, red iron oxide, yellow iron oxide, and bismuth oxychloride coated onto titanate treated hollow polyvinylidene chloride copolymer spheres.

One method of forming coated particles according to the invention is to add 0.01 to 5.0 weight percent (of particle weight), preferably 2%, of a liquid coupling agent to a uniform aqueous dispersion or slurry of particles at room temperature under rapid stirring conditions. At the end of 30 to 60 minutes stirring, an aqueous slurry of the coating material is added to the mixture while rapidly stirring. The mixture is stirred for an additional 20 to 60 minutes and the coated particles are then filtered off.

An alternate, less preferred, method of forming the coated particle of this invention comprises first spraying the liquid coupling agent onto a fluidized or agitated bed of base particles, and subsequently dispersing the coupling agent treated particles under rapid mixing conditions at room temperature so as to form an aqueous slurry or mixture. A slurry of coating material is added to the mixture, and is rapidly stirred at room temperature for 20 to 60 minutes. The coated particles are then filtered off from the mixture.

The following examples are given to illustrate the invention. Because these examples are given for illustrative purposes only, the invention should not be inferred to be limited to these examples.

EXAMPLE 1

Preparation of a Boron Nitride-Coated Polyvinylidene Chloride Copolymer Spheres

Two grams of isopropyl triisostearoyl titanate are added to a dispersion of 20 g of EXPANCEL 551 DE 20 in water using a Lightnin' type mixer. The addition of the titanate is done at room temperature accompanied by rapid stirring. Stirring is continued after addition of the titanate coupling agent for 60 minutes. A slurry of 78 g of Combat ® boron nitride powder, Grade SHP325, having a particle size of 30–40μ in water is then added to the mixture while rapidly stirring at room temperature. The resultant mixture is stirred for 60 minutes. The coated particles are then separated out of the mixture by filtering through a number 1 filter paper. The coated particles are then washed with water while still on the filter and then dried. The dried coated particle is then ground finely in a micropulverizer twice through a 0.020 inch screen to provide a product having a maximum particle size of 50μ.

EXAMPLE 2

Some typical boron nitride coated particles made in accordance with the invention are described in Table 1.

TABLE 1

Boron Nitride-Coated Particle

| Base Particle* | Wt % BN | Base Particle |
|---|---|---|
| Hollow spherical polyethylene; average particle size: 10μ | 97 | 3 |
| Starch; Dry Flo ®, National Starch, average particle size: 20μ | 35 | 65 |
| Alumina; average particle size: 8μ | 65 | 35 |
| Polymethylmethacrylate; 2-15μ | 35 | 65 |
| Nylon powder (5μ); hollow spheres | 35 | 65 |
| | 30 | 70 |
| Polyvinylidene chloride copolymer; 5-40μ | 85 | 15 |

*coated with 2% isopropyl triisostearoyl titanate

The boron nitride used in the compositions at Table 1 was Combat ®, grade SHP325. The particles were coated following the procedure described in Example 1, by first coating with the titanate coupling agent, followed by the boron nitride.

EXAMPLE 3

Powder Blush

| | % W/W |
|---|---|
| Mica 217 N-I2, Kobo Products, Inc., South Plainfield, New Jersey, comprising 70% mica having an average particle size of 5μ, coated onto 28% spherical Nylon having an average particle size of 5μ, the product having 2% isopropyl triisostearoyl titanate on the surface of the mica particles. | 15.00 |
| Pigment | |
| Iron Oxide Red | 2.00 |
| Iron Oxide Yellow | 0.24 |
| Iron Oxide Black | 0.40 |
| D+C Red #30 Al. Lake | 0.75 |
| Ultra Marine Blue | 0.58 |
| 20% polyvinylidene chloride copolymer (20μ) coated with 78% boron nitride, and 2% isopropyl triisostearoyl titanate, according to Example 1 above. | 0.30 |
| Titanium dioxide/mica (titanated mica) | 10.00 |
| Dimethicone/dimethiconol | 6.0928 |
| Dimethicone/trimethylsiloxysilicate | 0.64 |
| Triisocetyl citrate | 0.40 |
| Polysiloxane polyalkylene copolymer | 0.80 |
| Methyldibromo glutaronitrile/ phenoxyethanol | 0.0672 |
| Polytetrafluoroethylene; Ceridust 9205F; Hoechst-Celanese Corp. | 8.27 |
| Zinc Stearate | 3.00 |
| Fragrance | 0.15 |
| Mica; Sericite 281 ®; Whittaker, Clark & Daniels | 51.31 |
| | 100.00 |

The powder blush is prepared by mixing all of the ingredients except for binder in a Baker-Perkins at a controlled temperature of 40° C. for about 20 minutes. The batch is then dropped from the mixer and pulverized by passage through a Micropulverizer having a 0.020 inch screen the batch is again placed in the Baker-Perkins and the binder is then added slowly over a 15 minute period while mixing at 40° C. After mixing is completed, the product is dropped from the mixer, again passed through the micropulverizer with 0.020 inch screen and then compressed into a cake using 4000 psi pressure to provide a product having excellent characteristics.

EXAMPLE 4

Spherical Silica Coated on to Polyvinylidene Chloride Copolymer Base Particles

Two grams of isopropyl triisostearoyl titanate are added to a slurry of 20 g of EXPANCEL 551 DE 20, having a particle size of 20μ max. and a density less than 0.1 gm/cm³, in water with rapid stirring at room temperature. The resultant mixture is stirred for 60 minutes. 78 g of MSS-500, a spherical silica having an average particle size of 10μ sold by Kobo Products, Inc., South Plainfield, N.J., is then added to the resultant mixture while stirring and the stirring is continued for 60 minutes. The coated particles are then separated out of the mixture by filtering through a number 1 paper. The coated particles are then washed while still on the filter and then dried. The dried coated particle is then ground finely in a micropulverizer twice through a 0.020 inch screen.

EXAMPLE 5

Pressed Eyeshadow

| | % W/W |
|---|---|
| Lauroyl Lysine-Coated Mica | 20.00 |
| Boron Nitride (8μ) | 1.50 |
| Polytetrafluoroethylene; Ceridust 9205F; Hoechst-Celanese Corp. | 5.00 |
| Iron Oxide Yellow | 0.64 |
| Iron Oxide Red | 0.28 |
| Carmine | 0.14 |
| Titanium Dioxide | 1.24 |
| Triisoarachidyl Citrate | 1.95 |
| Dioctyl Maleate | 1.25 |
| Tridecyl Neopentanoate | 1.30 |
| Octyl Dodecyl Stearoyl Stearate | 1.95 |
| 20% polyvinylidene chloride copolymer 20μ, treated with 2% isopropyl triisostearoyl titanate and coated with 78% spherical silica, as described in Example 4 | 1.50 |
| Magnesium Stearate | 3.00 |
| Methyldibromoglutaronitrile/ phenoxyethanol | 0.05 |
| Talc coated with 3% Trimyristin | 60.20 |
| | 100.00 |

The pressed eye shadow is prepared by mixing all of the ingredients except for binder and fragrance until uniform, (about 20 minutes) in a Baker-Perkins at a controlled temperature of 40° C. The binder and fragrance are then added slowly while mixing is continued for another 15 minutes at 40° C., after which the mixture is dropped from the mixer and milled twice through a 0.020 inch screen. The final product is compressed at a pressure of about 1000 psi into a rectangular metal pan, to form a cake suitable for packaging. The blush readily adheres to the skin of the user and has excellent tactile properties.

It is noted that boron nitride-coated spheres made according to Example 1 are employed at a level of 0.3% without causing problem of loss of cake compression during storage. Where a simple mixture of boron nitride and polyvinylidine chloride hollow spheres are employed, the spheres can be used only at a level of 0.1% in this formula without loss of cake compression during storage.

EXAMPLE 6

Pressed Powder

|  | % W/W |
|---|---|
| Polytetrafluoroethylene; Ceridust 9205F | 0.90 |
| Mica 217 N-I2, Kobo Products, Inc. | 15.00 |
| Lithium Stearate | 2.00 |
| Iron Oxide Black | 0.16 |
| Iron Oxide Yellow | 0.35 |
| Iron Oxide Red | 0.26 |
| Zinc Palmitate | 3.50 |
| High Density Polyethylene | 5.00 |
| Boron Nitride (8μ) | 1.00 |
| 20% Polyvinylidene chloride Copolymer coated with 78% Boron Nitride, 2% Isopropyl Triisostearoyl Titanate, prepared according to Example 1 | .30 |
| Triisocetyl Citrate | 0.37725 |
| Mica | 29.10 |
| Dimethicone/Dimethiconol | 6.405751 |
| Dimethicone/Trimethylsiloxysilicate | 0.654 |
| Phenoxyethanol | 0.0504 |
| Methyldibromo Glutaronitrile | 0.0126 |
| Talc coated with 3% trimyristin | 34.92999 |
|  | 100.00 |

The pressed powder cosmetic is prepared by mixing all of the ingredients except for binder in a Baker-Perkins blender at a controlled temperature of 40° C. for about 20 minutes. The binder is added slowly over a 15 minute period while mixing at 40° C. The batch is then dropped from the mixer and pulverized by passage through a micropulverizer having a 0.020 inch screen. The batch is then compressed into cakes using 2000 psi pressure to provide a pressed powder having excellent characteristics.

We claim:

1. A coated particle for use in cosmetic preparations comprising a base particle having an outer surface, a first coating of coupling agent selected from the group consisting of silanes and titanates overlying said outer surface, and second coating of boron nitride overlying said first coating, wherein said boron nitride is present in the amount of 50-99% by weight of said coated particle.

2. A coated particle according to claim 1 wherein said coupling agent is isopropyl triisostearyl titanate.

3. A coated particle according to claim 2 wherein said base particle is selected from the group consisting of polyamide, starch, polymethylmethacrylate, low density polyethylene, silica, polyvinylidene chloride copolymer and polystyrene.

4. A coated particle according to claim 3 wherein said base particle is polyamide.

5. A coated particle according to claim 3 wherein said base particle is starch.

6. A coated particle according to claim 3 wherein said base particle is silica.

7. A coated particle according to claim 3 wherein said base particle is a polyvinylidene chloride copolymer.

8. A coated particle according to claim 7 where said base particle has a particle size of 20-40μ and a density of 0.01 to 0.065 gm/cm$^3$.

9. A coated particle according to claim 2 wherein said coated particle has a particle size of 5-80μ.

10. A method of forming coated particles for use in cosmetic preparations comprising applying a first coating of coupling agent to a base particle wherein said coupling agent is present in the amount of 0.01 to 5.0 weight % based upon base particle weight and is selected from the group consisting of silanes and titanates, and applying a second coating of boron nitride to overlie said first coating wherein said boron nitride is present in the amount of 50-99% by weight of said coated particle.

11. A method according to claim 10 wherein said coupling agent is isopropyl triisostearoyl titanate.

12. A method according to claim 11 wherein said base particle is selected from the group consisting of polyamide, starch, polymethylmethacrylate, polyethylene, silica, polyvinylidene chloride copolymer and polystyrene.

13. A method according to claim 12 wherein said base particle is polyamide.

14. A method according to claim 12 wherein said base particle is starch.

15. A method according to claim 12 wherein said base particle is silica.

16. A method according to claim 12 wherein said base particle is a polyvinylidene chloride copolymer.

17. A method according to claim 16 wherein said base particle has a particle size of about 20-40μ and a density of 0.01 to 0.065 gm/cm$^3$.

18. A cosmetic preparation comprising the coated particle of claim 1.

* * * * *